United States Patent
Ozaki et al.

(10) Patent No.: US 10,313,422 B2
(45) Date of Patent: Jun. 4, 2019

(54) CONTROLLING A DEVICE BASED ON LOG AND SENSOR DATA

(71) Applicant: Hitachi, Ltd., Tokyo (JP)

(72) Inventors: Hiroaki Ozaki, Mountain View, CA (US); Abhay Mehta, Austin, TX (US); Hsiu-Khuern Tang, San Jose, CA (US); Shuang Feng, Milpitas, CA (US); Haiyan Wang, Fremont, CA (US)

(73) Assignee: Hitachi, Ltd., Tokyo (JP)

( * ) Notice: Subject to any disclaimer, the term of this patent is extended or adjusted under 35 U.S.C. 154(b) by 205 days.

(21) Appl. No.: 15/294,826

(22) Filed: Oct. 17, 2016

(65) Prior Publication Data

US 2018/0109589 A1    Apr. 19, 2018

(51) Int. Cl.

| | |
|---|---|
| *H04L 29/08* | (2006.01) |
| *H04L 12/26* | (2006.01) |
| *G06F 19/00* | (2018.01) |
| *G06N 3/08* | (2006.01) |
| *G16H 50/20* | (2018.01) |
| *G16H 40/60* | (2018.01) |

(52) U.S. Cl.
CPC .......... *H04L 67/025* (2013.01); *G06F 19/00* (2013.01); *G06N 3/08* (2013.01); *G16H 40/60* (2018.01); *G16H 50/20* (2018.01); *H04L 43/10* (2013.01); *H04L 67/306* (2013.01)

(58) Field of Classification Search
USPC ...................................................... 709/223
See application file for complete search history.

(56) References Cited

U.S. PATENT DOCUMENTS

| | | | |
|---|---|---|---|
| 2009/0006061 A1* | 1/2009 | Thukral ............... | G06F 19/325 703/11 |
| 2009/0006129 A1* | 1/2009 | Thukral ............. | G06F 19/3456 705/2 |
| 2012/0259648 A1* | 10/2012 | Mallon ............... | G06F 19/3418 705/2 |

(Continued)

FOREIGN PATENT DOCUMENTS

| | | |
|---|---|---|
| EP | 1596334 A1 | 11/2005 |
| WO | 2013/003905 A1 | 1/2013 |

OTHER PUBLICATIONS

Extended European Search Report received in corresponding European Application No. 17196821.7 dated Mar. 16, 2018.

*Primary Examiner* — Jude Jean Gilles
(74) *Attorney, Agent, or Firm* — Mattingly & Malur, PC

(57) ABSTRACT

In some examples, a computing device may receive sensor data for a target and at least one of: log data for the target, or historical log data and historical sensor data for a plurality of other targets. The computing device may determine at least one event classified as a non-uniform event in at least one of the log data or the historical log data, and may determine combined features, such as a feature vector, based on the sensor data and the non-uniform event(s). The computing device may determine an analysis result from the combined features. Further, based on the analysis result, the computing device may send a control signal to a device associated with the target for controlling the device, and/or may send a communication related to the target to another computing device.

20 Claims, 11 Drawing Sheets

(56) References Cited

U.S. PATENT DOCUMENTS

| | | | |
|---|---|---|---|
| 2012/0259649 A1* | 10/2012 | Mallon | G06Q 10/06 |
| | | | 705/2 |
| 2012/0259651 A1* | 10/2012 | Mallon | G06Q 10/06 |
| | | | 705/2 |
| 2012/0290521 A1 | 11/2012 | Frank et al. | |
| 2012/0323087 A1 | 12/2012 | Villeda et al. | |
| 2013/0204640 A1* | 8/2013 | Underdal | G06Q 10/00 |
| | | | 705/3 |
| 2014/0019450 A1 | 1/2014 | Rus et al. | |
| 2014/0142442 A1* | 5/2014 | Snow | A61B 5/7405 |
| | | | 600/485 |
| 2014/0155763 A1* | 6/2014 | Bruce | A61B 5/7221 |
| | | | 600/484 |
| 2017/0004260 A1* | 1/2017 | Moturu | G06F 19/3418 |
| 2017/0112434 A1* | 4/2017 | Lane | A61B 5/4848 |
| 2017/0112451 A1* | 4/2017 | Meyerson | A61B 5/0205 |
| 2018/0060492 A1* | 3/2018 | Feng | G06F 17/30598 |

* cited by examiner

| TARGET ID | TIME | DESCRIPTION |
|---|---|---|
| 1001 | 2016-05-19 04:10:00 | HEAD OF BED AT 30 DEGREES |
| ... | ... | ... |
| 2501 | 2016-05-19 15:20:00 | READY TO WEAN FROM VENTILATOR |
| ... | ... | ... |

FIG. 2

| TARGET ID | TIME | SENSOR NAME | UNIT | VALUE |
|---|---|---|---|---|
| 1001 | 2016-05-19 03:05:00 | SpO2 | PERCENT | 95 |
| ... | ... | ... | ... | ... |
| 2501 | 2016-05-01 16:49:00 | BLOOD PRESSURE | MMHG | 120/75 |
| ... | ... | ... | ... | ... |

FIG. 3

CONTROLLING A DEVICE BASED ON LOG AND SENSOR DATA

BACKGROUND

Patients in hospitals and other medical care facilities frequently may be connected to, or otherwise monitored by, a plurality of different types of medical devices that monitor various bodily conditions. Each of these monitors may include one or more sensors and processing components that provide information about the patient. Additionally, patients may be treated by medical devices that provide treatment for one or more medical conditions. These devices also may provide sensor data indicative of their operation. Furthermore, caregivers, such as nurses, physicians, physician assistants, and other medical professionals may also record log information about a patient as patient log data. The patient log data may contain human decisions and diagnosis of patient status. Examples of information that may be included in the patient log data may include patient treatments, patient conditions, prognoses, treatment plans, types of medication, frequency of medication, tests performed, caregiver observations, and so forth.

Despite the tremendous amount of available data, treatment of patients is often performed based on predetermined treatment regimens that may be manually managed by caregivers. For instance, caregivers may be responsible for manually turning on and off treatment devices and other medical devices. Additionally, caregiver judgment typically may be used for determining timing and frequency for applying treatment to a particular patient. However, caregivers may not be able to take into consideration all available data when determining types of treatments, timing of treatments, prognoses for a patient, long-term care plans, likelihood of readmission, or the like.

SUMMARY

Some implementations include arrangements and techniques for performing analysis, sending notifications, making determinations, and/or controlling devices based on analysis of sensor data and log data. In some examples, a computing device may receive sensor data for a target and at least one of: log data for the target; or historical log data and historical sensor data for a plurality of other targets. The computing device may determine at least one event classified as a non-uniform event in at least one of the log data or the historical log data, and may determine combined features, such as a feature vector, based on the sensor data and the at least one non-uniform event. The computing device may determine an analysis result from the combined features based on at least one of regression or classification applied to the features. Further, based on the analysis result, the computing device may send a control signal to a device associated with the target for controlling the device, and/or may send a communication related to the target to another computing device.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 2 illustrates an example data structure including log data according to some implementations.

FIG. 3 illustrates an example data structure representative of sensor data according to some implementations.

DETAILED DESCRIPTION

Figure 1:
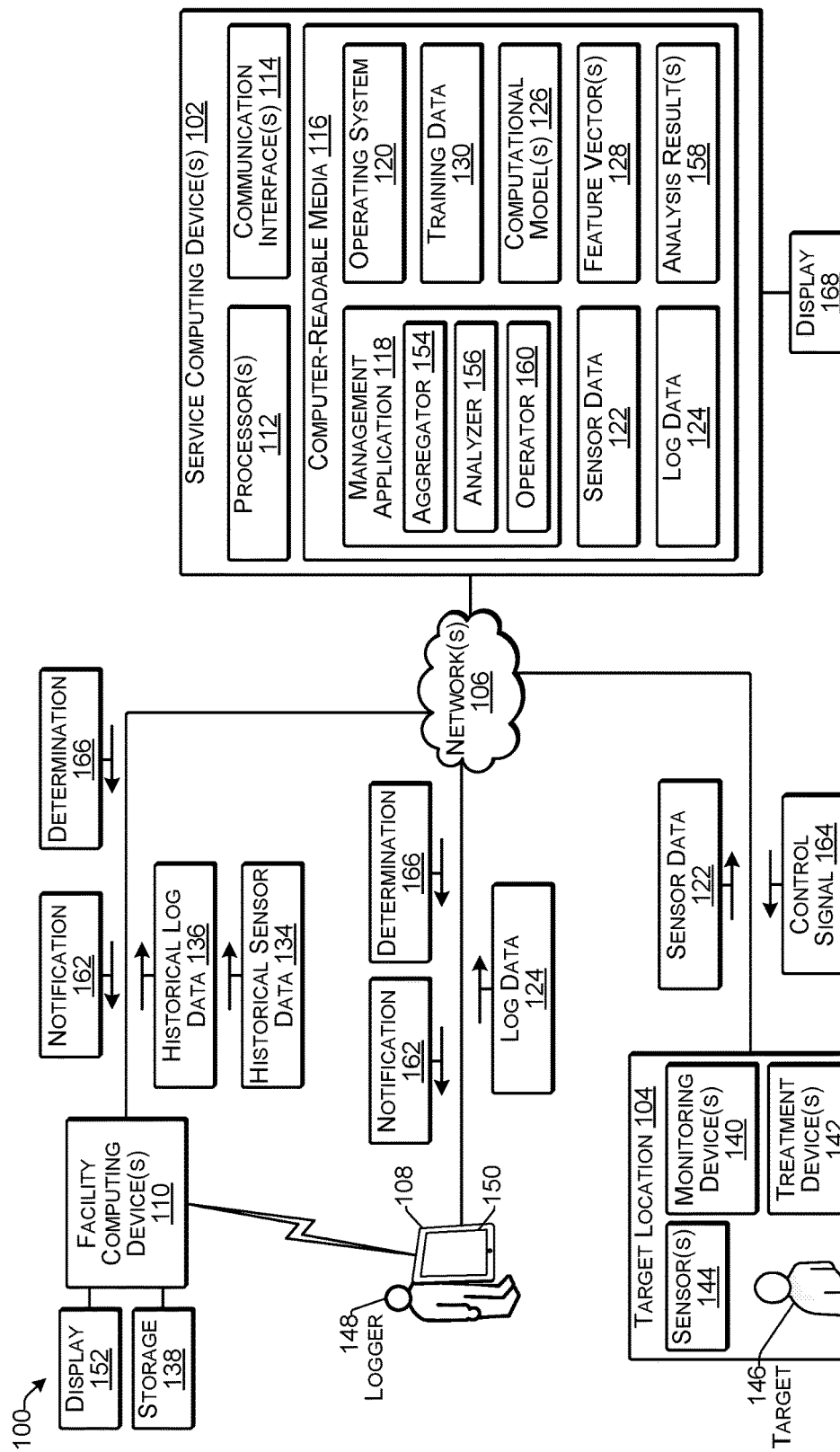
FIG. 1 illustrates an example architecture of a system able to control a device and/or provide a notification or other information as output according to some implementations.

Some implementations herein are directed to techniques and arrangements for considering sensor data and log data for making determinations with respect to operation of treatment devices and/or for making determinations regarding patient care. As one example, sensor data from patient devices and patient log data from caregivers may be received as data inputs. The log data and the sensor data may be analyzed together based at least partially on data from one or more non-uniform events from the log data. Combined features, such as a feature vector, may be determined either directly from received data, or indirectly by using a statistical model or neural network that provides the combined features as an output. For instance, the features may be determined at least partially based on occurrences of non-uniform events, which may correspond to changes of state of the target. The features may be combined by aggregating based on similar states, and in some examples, the aggregated features may be concatenated as feature vectors. The combined features may be used for determining an analysis result. The analysis result may be used by a management application for performing an action, such as turning on or off a treatment device, changing a setting on a treatment device, sending an alert or other notification to a caregiver, making a determination about patient treatment effectiveness, making a determination about patient prognosis, or the like.

In some examples, the management application may cluster and or otherwise classify patient log data into one of two event classifications: uniform events and non-uniform events. Based on this classification, log data that is classified as a uniform event may be excluded and may not be used for generating the combined features, while log data that is classified as non-uniform events may be used when generating the combined features because this data may correspond to points in time at which a patient status may have changed. Accordingly, features may be formed, combined, or otherwise determined using non-uniform data to determine points of interest. Furthermore, several different analysis techniques may be applied, including direct data segmentation based on the change points and indirect data segmentation using states from statistical models or artificial neural networks.

Some implementations herein may provide a prediction and/or estimations for making determinations about target patients, such as whether a patient will be in danger of respiratory failure in the near future, whether the patient is being cared for correctly, and so forth. Two types of data may be employed for analysis, with the first type being sensor data including sensor measurement information from one or more sensors, and the second type being patient log data including logged caregiver notes, observations, and other records related to patient treatments and conditions. Implementations herein may control patient treatment devices or provide other output regarding a patient using machine learning technology based on comprehensive feature vectors determined from the sensor data and manually-entered log data.

Some implementations may enable a computing device performing the analysis herein to make determinations regarding a patient's condition that are more accurate than if sensor data alone were relied upon. Furthermore, medical devices or other target devices that are controlled based on the analysis results herein may be controlled more accurately. As one example, suppose that the estimated results include an estimation of the respiratory status of a patient who is on a mechanical ventilator. The computing device herein may control the ventilator setting, such as by changing an inspiratory pressure setting for the ventilator, or otherwise controlling the ventilator based on the estimated respiratory status of the patient.

For discussion purposes, some example implementations are described in the environment of one or more computing devices that receive data, such as sensor data and log data, and determine features from the data to provide an output, such as a notification sent to a caregiver computing device and/or a control signal sent for controlling a target device. However, implementations herein are not limited to the particular examples provided, and may be extended to other types of data, other types of environments, other system architectures, other types of computational models, and so forth, as will be apparent to those of skill in the art in light of the disclosure herein. For instance, while some examples are described in the environment of providing medical care to a patient, implementations herein are not limited to this environment, and may be extended to other environments for determining an output useful for controlling a device, for providing a notification, for making a determination, or the like.

FIG. 1 illustrates an example architecture of a system 100 able to control a device and/or provide a notification or other information as output according to some implementations. The system 100 includes a least one service computing device 102 that is able to communicate with one or more target locations 104, such as through one or more networks 106. Further, the service computing device 102 may be able to communicate through the one or more networks 106 with one or more logger computing devices 108 and one or more facility computing devices 110.

In some examples, the service computing device 102 may include one or more servers, personal computers, or other types of computing devices that may be embodied in any number of ways. For instance, in the case of a server, the modules, other functional components, and at least a portion of data storage may be implemented on at least one server, such as in a cluster of servers, a server farm or data center, a cloud-hosted computing service, and so forth, although other computer architectures may additionally or alternatively be used. In the illustrated example, the service computing device 102 includes, or may have associated therewith, one or more processors 112, one or more communication interfaces 114, and one or more computer-readable media 116.

Each processor 112 may be a single processing unit or a number of processing units, and may include single or multiple computing units, or multiple processing cores. The processor(s) 112 can be implemented as one or more central processing units, microprocessors, microcomputers, microcontrollers, digital signal processors, state machines, logic circuitries, and/or any devices that manipulate signals based on operational instructions. For instance, the processor(s) 112 may be one or more hardware processors and/or logic circuits of any suitable type specifically programmed or configured to execute the algorithms and processes described herein. The processor(s) 112 can be configured to fetch and execute computer-readable instructions stored in the computer-readable media 116, which can program the processor(s) 112 to perform the functions described herein.

The computer-readable media 116 may include volatile and nonvolatile memory and/or removable and non-removable media implemented in any type of technology for storage of information such as computer-readable instructions, data structures, program modules, or other data. For example, the computer-readable media 116 may include, but is not limited to, RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the service computing device 102, the computer-readable media 116 may be a tangible non-transitory medium to the extent that, when mentioned, non-transitory computer-readable media exclude media such as energy, carrier signals, electromagnetic waves, and/or signals per se. In some cases, the computer-readable media 116 may be at the same location as the service computing device 102, while in other examples, the computer-readable media 116 may be partially remote from the service computing device 102.

The computer-readable media 116 may be used to store any number of functional components that are executable by the processor(s) 112. In many implementations, these functional components comprise instructions or programs that are executable by the processor(s) 112 and that, when executed, specifically program the processor(s) 112 to perform the actions attributed herein to the service computing device 102. Functional components stored in the computer-readable media 116 may include a management application 118 and an operating system (OS) 120. The management application 118 may include one or more computer programs, computer-readable instructions, executable code, or portions thereof that are executable to cause the processor(s) 112 to performing various tasks, such as for receiving and analyzing patient data, monitoring patient status, providing alerts, information, or other notifications to caregivers, and/or for controlling target devices. Additionally, the operating system 120 may control and manage various functions of the service computing device 102. In some cases, the functional components may be stored in a storage portion of the computer-readable media 116, loaded into a local memory portion of the computer-readable media 116, and executed by the one or more processors 112. Numerous other software and/or hardware configurations will be apparent to those of skill in the art having the benefit of the disclosure herein.

In addition, the computer-readable media 116 may store data and data structures used for performing the functions and services described herein. For example, the computer-readable media 116 may store sensor data 122, log data 124, one or more computational models 126, combined features, such as one or more feature vectors 128, and training data 130 that may be used by the management application 118. For example, the management application 118 may receive the sensor data 122 and the log data 124 related to one or more patients, and may use this information to determine combined features, such as the one or more feature vectors 128, either directly or indirectly, using one or more computational models 126, such as statistical models and/or neural networks. The feature vectors 128 may be used to determine information about the respective patients.

As discussed additionally below, the management application 118 may use determinations made from the feature vectors 128 to perform functions such as controlling target devices, sending alerts or other notifications to caregivers, monitoring patient care, predicting patient outcomes, or the like. In some examples, the training data 130 may include historical sensor data 134 and historical log data 136 stored for a plurality of patients, and which may be received from a database or other storage 138 associated with the facility computing device(s) 110. The training data 130 may be used to train the computational model(s) 126, which may then be executed for sensor data 122 and, in some examples, log data 124, received for a particular target, such as a current patient. The service computing device 102 may also include or maintain other functional components and data, which may include programs, drivers, etc., and other data used or generated by the functional components. Further, the service computing device 102 may include many other logical, programmatic, and physical components, of which those described above are merely examples that are related to the discussion herein.

The communication interface(s) 114 may include one or more interfaces and hardware components for enabling communication with various other devices, such as over the one or more networks 106. Thus, the communication interfaces 114 may include, or may couple to, one or more ports that provide connection to the network(s) 106 for communicating with the target location(s) 104, the logger computing device(s) 108, and the facility computing device(s) 110. For example, the communication interface(s) 114 may enable communication through one or more of a LAN (local area network), WAN (wide area network), the Internet, cable networks, cellular networks, wireless networks (e.g., Wi-Fi) and wired networks (e.g., fiber optic, Ethernet, Fibre Channel), direct connections, as well as close-range communications such as BLUETOOTH®, and the like, as additionally enumerated elsewhere herein.

The one or more networks 106 may include any type of network, including LAN, such as an intranet; a WAN, such as the Internet; a wireless network, such as a cellular network, a local wireless network, such as Wi-Fi, and/or short-range wireless communications, such as BLUETOOTH®; a wired network including fiber optics, Ethernet, Fibre Channel, or any other such network, a direct wired connection, or any combination thereof. Accordingly, the one or more networks 106 may include both wired and/or wireless communication technologies. Components used for such communications can depend at least in part upon the type of network, the environment selected, or both. Protocols for communicating over such networks are well known and will not be discussed herein in detail. Accordingly, the service computing device 102, the target location(s) 104, the logger computing device(s) 108, and the facility computing device(s) 110 are able to communicate over the one or more networks 106 using wired or wireless connections, and combinations thereof.

The target location 104 may be a patient room or any other location where a patient or other monitored target may be located. In some examples, each of the target locations 104 may include a plurality of target devices that may include one or more patient monitoring devices 140 and/or one or more patient treatment devices 142. Further, sensors 144 may be associated with the monitoring device(s) 140 and/or the treatment device(s) 142, such as for detecting patient conditions and/or conditions of the monitoring devices 140 and/or the treatment devices 142. As one example, at least one patient or other monitored target 146 may be located at each of the target locations 104, may be monitored by the monitoring device(s) 140, and may be treated by the treatment device(s) 142. Further, in some cases, a treatment device 142 may also be a monitoring device 140, and may include one or more of the sensors 144 for providing sensor data about the target patient's condition. For instance, the management application 118 may use received sensor data 122 and, in some examples, log data 124 received about the particular target 146 for analyzing the target 146 to control a treatment device 142 or a monitoring device 140 at the target location 104.

In some examples, each of the target devices 140, 142 may be able to communicate over the network 106 with the service computing device 102, such as to send sensor data 122 to the service computing device 102. In other examples, one of the target devices 140, 142 may include a computing device that collects the sensor data 122 from other target devices 140, 142 at the target location 104, and that sends the sensor data 122 to the service computing device 102 and/or the facility computing device 110. As several examples, the patient monitoring devices 140 may include cardiac monitors, pulse oximeters, capnography monitors, respiratory rate monitors, neurological monitors, blood glucose monitors, fetal monitors, body temperature monitors, hemodynamic monitors, and/or various other types of monitoring devices. Further, the patient treatment devices 142 may include ventilators, intravenous (IV) infusion pumps, pacemakers, chest tubes, feeding tubes, anesthetic machines, heart-lung machines, dialysis machines, urinary catheters, defibrillators, and/or various other types of treatment devices.

The logger computing device(s) 108 and the facility computing device(s) 110 may be any suitable type of computing devices such as a desktop, workstation, server, laptop, tablet computing device, mobile device, smart phone, wearable device, or any other type of computing device able to send data over a network. In some cases, the logger computing device 108 and/or the facility computing device 110 may include hardware configurations similar to that described for the service computing device 102, but with different data and functional components to enable them to perform the various functions discussed herein. As one example, the logger computing device 108 may be a portable computing device, such as a tablet or laptop that a caregiver or other logger 148 carries when visiting target locations 104, and the facility computing device 110 may be a server, workstation, desktop computer, e.g., located onsite at a care facility or at another location.

In some cases, the facility computing device 110 may be a server that stores patient records in the storage 138, which may include historical log data 136 and historical sensor data 134 collected in the past for a plurality of patients, and which may be used as the training data 130 for one or more statistical models or neural networks. Further, in some examples, one or more of the facility computing devices 110 may include a monitoring computing device, such as at a central location in a care facility where the target location 104 is located, e.g., at an ICU, or the like, to enable monitoring of individual patients at the care facility. The logger computing device 108 may include a display 150, and the facility computing device(s) 110 may include a display 152. Numerous other variations will be apparent to those of skill in the art having the benefit of the disclosure herein.

In some examples, the logger 148 may be a caregiver, such as a nurse, physician, physician's assistant, attendant, or other medical professional, may visit the patient(s) 146 at the target location(s) 104, and may use the logger computing device 108 to enter or otherwise generate the log data 124 for a particular target 146. For instance, the log data 124 may be related to the patient's condition, the settings or output of the patient monitoring devices 140, the settings or output of the patient treatment devices 142, caregiver observations, and so forth. In some examples, the log data 124 may be entered in a structured manner as structured data, such as by enabling the logger 148 to make selections in a form, or the like. Alternatively, in other examples, the log data 124 may be handwritten records, typed records, or otherwise freeform data that may be analyzed by the service computing device 102 or the facility computing device 110 following receipt thereby. The log data 124 may be sent to the service computing device 102 by each logger computing device 108, such as when entered by the logger 148, when the logger 148 has finished seeing a particular target 146, at the end of the logger's shift, or the like. In some cases, the log data 124 may be first sent to the facility computing device 110 and from there may be sent to the service computing device 102. Similarly, in some examples the facility computing device 110 may first receive the sensor data 122 and may forward the sensor data 122 to the service computing device 102.

In the example of FIG. 1, the management application 118 may be executed to receive the historical sensor data 134 and the historical log data 136 as the training data 130. For example, management application 118 may include an aggregator 154 that receives and aggregates sensor data 122 and log data 124 related to particular targets 146. For example, the aggregator 154 may receive and store sensor data 122 and log data 124 in relationship to a particular target identifier (ID), such as a patient ID, that may be individual distinguishable in the system from other target IDs. In some example, the aggregator may restructure the received data to a particular format. For instance, in the case of the log data, the aggregator may extract information related to particular events, as discussed additionally below.

The management application 118 may further include an analyzer 156 that provides analysis to predict and/or estimate one or more values that may be used for making a determination with respect to the target 146. The analyzer 156 may generate at least one feature vector 128 from the sensor data 122 and the log data 124, and may use the feature vector 128 to make a prediction and/or estimation as an analysis result 158. In some examples, the analyzer 156 may determine features directly from the sensor data 122 and the log data 124. In other examples, the analyzer 156 may use the training data 130 to train one of the computational models 126, such as a statistical model or neural network, and may subsequently execute the trained computational model by applying at least the received sensor data 122 related to a particular target 146 to obtain a feature vector 128. The feature vector 128 may then be used in further analysis to determine one or more analysis results 158.

The management application 118 may further include an operator 160 that may receive the analysis result 158 obtained by the analyzer 156 using the feature vector 128, and may perform at least one operation based on the analysis result 158. The analysis result 158 may further be stored by the analyzer 156 in the computer-readable media 116 and/or at the storage 138, such as in a database or other storage architecture. In some cases, the analysis results 158 may be stored in the form of a log or sensor measurement data associated with the particular target patient (e.g., by target ID).

After the analyzer 156 determines the analysis result 158, the operator 160 of the management application 118 may receive the analysis result 158 and may perform an operation based on the analysis result 158, such as sending an alert or other notification 162 to at least one of the logger computing device 108 or the facility computing device(s) 110. For instance, the notification 162 may be presented on the display 150 and/or 152 respectively, to notify the logger 148, another caregiver or other medical personnel of a patient condition.

Additionally, or alternatively, the operator 160 of the management application 118 may automatically adjust a setting of one or more target devices 140, 142, such as by sending a control signal 164 for controlling a particular patient treatment device 142 or a particular patient monitoring device 140. Thus, the analysis results 158 may be used as feedback for controlling a target device. For example, if the target device is a ventilator, the control signal may adjust a pressure setting of the ventilator to control more accurately the ventilator based on collected and analyzed information about the target 146. As another example, suppose that the target device is an IV infusion pump, and the analysis results 158 indicate that the patient is receiving too much IV fluid. The control signal 156 may control the infusion pump to decrease the flow of IV fluid to the patient, thereby providing improved operation of the infusion pump. As another example, the control signal 156 may control a monitoring device 140, such as to turn on a particular monitoring device 140 that may not have been on, but which may be used to further monitor the target patient based on an indicated patient condition indicated by the analysis result 158. Accordingly, based on the analysis result 158, the management application 118 may send a control signal to a device associated with the target for controlling the device in response to a condition indicated by the analysis result.

Furthermore, in some cases, the analysis result 158 may be used by the management application 118 to make a determination 166 about the target 146, such as a diagnosis, a prognosis, a prediction of the efficacy of treatment, a prediction as to whether the patient will have to be readmitted to the care facility if released, or the like. The operator 160 of the management program 118 may send this determination 166 to at least one of the logger computing device 108 or the facility computing device 110. In addition, the analysis result 158 may be presented on a display 168 associated with the service computing device 102, such as in a graphic user interface (GUI), or the like.

The computational model(s) 126 may be periodically updated and re-trained based on new training data 130 to keep the computational model(s) 126 up to date. Examples of suitable computational models 126 that may be used in some implementations herein may include predictive models, decision trees, classifiers, regression models, such as linear regression models, support vector machines, and stochastic models, such as Markov models and hidden Markov models, artificial neural networks, such as recurrent neural networks, long short term memory (LSTM) neural networks, and so forth. Accordingly, implementations herein are able to provide predictions and/or estimations according to the log data and sensor data. Further, in some cases, the data may be processed in a streaming manner, i.e., as the data is received at the service computing device 102. In other cases, the data may be process as batch processing, i.e., after a batch of data is accumulated by the service computing device 102. The analysis result 158 may provide status information regarding a particular target and can provide feedback for controlling a target device.

FIG. 2 illustrates an example data structure 200 including log data according to some implementations. In this example, data structure 200 is a table that includes log data such as may be received from a logger computing device 108, or the like. The data structure 200 includes a target ID 202, such as a patient ID, time information 204, and descriptions 206. Each row in the data structure 200 may correspond to a single observation of a patient status, and thus, multiple rows may be included for each target ID 202. Accordingly, the target ID may be used to aggregate log data for a particular patient. The time 204 represents the date and time at which the corresponding log data was recorded or observed. Further, the description column 206 may include logged information about the target status, such as in text format or other structured or unstructured format, as discussed above.

FIG. 3 illustrates an example data structure 300 representative of sensor data according to some implementations. In this example, the data structure 300 is a table that includes sensor measurements. The data structure 300 includes a target ID 302, such as a patient ID, time 304, a sensor name 306, sensed information unit 308, and sensed information value 310. Each row corresponds to one measurement of single sensor. The target ID 302 indicates the patient with whom the data is associated. The time 304 indicates the date and time at which the data was recorded or observed. The sensor name 306 indicates the type of sensor from which the data was received. The unit 308 indicates a unit of measurement used for the sensed value 310. The data structure 300 may be populated as sensor data is received from one or more target locations. Further, additional data structures may be constructed, such as for separating the received sensor data according to target ID. By forming the data structures 200 and 300 as described above, any types of data may be handled without having to take into consideration how many types of data are available, which makes the system flexible for handling changing types of sensor data and log data.

Figure 4:
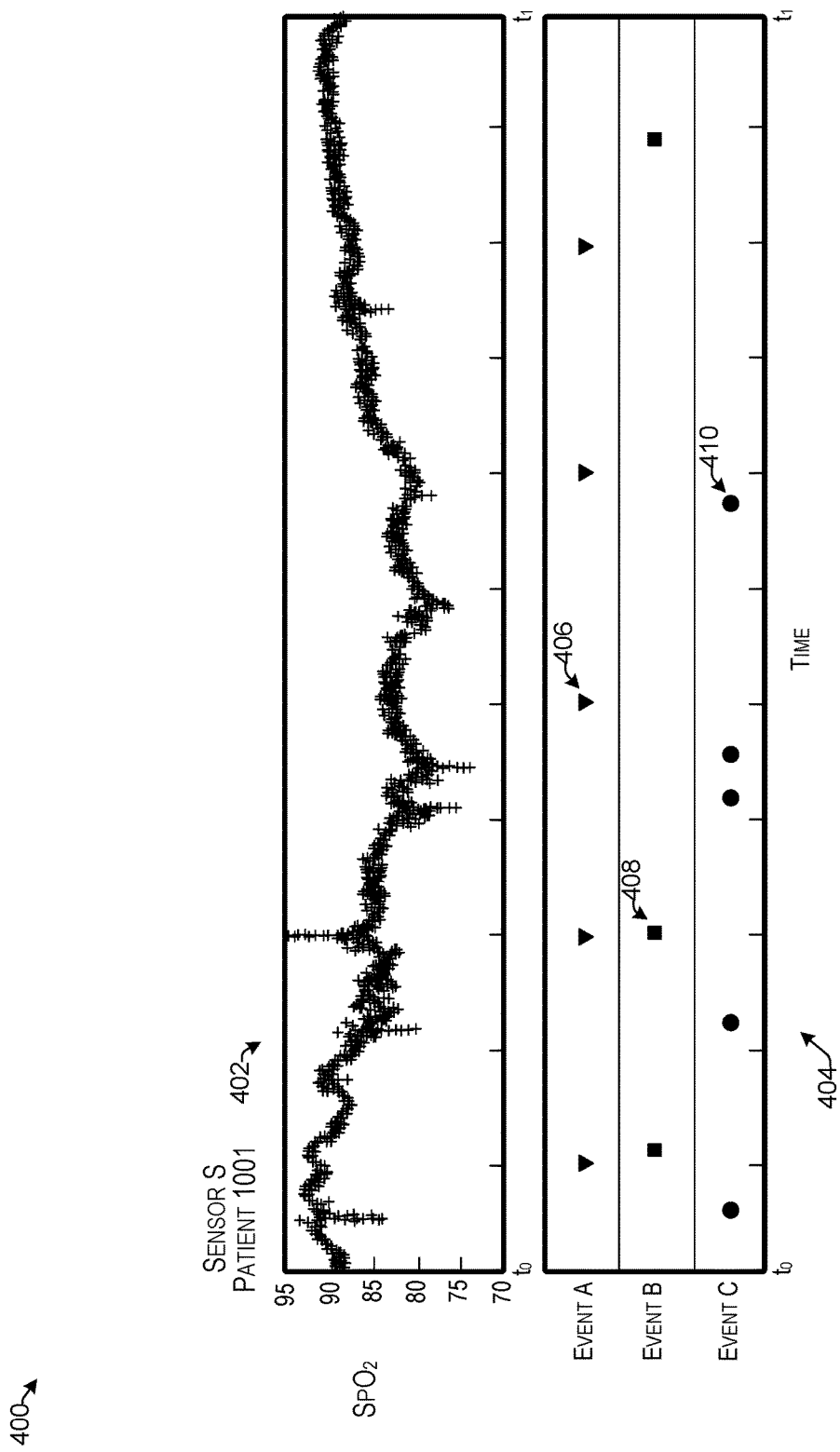
FIG. 4 illustrates an example of sensor data and log data according to some implementations.

FIG. 4 illustrates an example 400 of sensor data and log data according to some implementations. In this example, a graph 402 illustrates a sample of sensor data received from sensor S for a particular target patient having a patient ID 1001. The graph 402 illustrates a plurality of measurements of blood oxygen saturation in percent over a selected window of time from $t_0$ to $t_1$ for patient 1001. In some examples, the selected time window may be static, while in other examples, the time window may be a moving or growing window as new sensor data and log data is received. Further, while blood oxygen sensor data is used in this example, data from numerous other types of sensors may be used in addition to, or as an alternative to blood oxygen sensor data.

In addition, a graph 404 illustrates occurrences of events A, B, and C over the window of time from $t_0$ to $t_1$, as determined from received log data for the patient 1001. Since the events are determined from log data, each event A, B, and C may have sparse occurrences compared to the sensor data illustrated in graph 402. For instance, occurrences of event A are indicated by inverted triangles 406, occurrences of event B are indicated by squares 408, and occurrences of event C are indicated by circles 410.

In some examples, uniform events are filtered out or otherwise excluded from the log data that is used for analysis. For example, event A is an example of a uniform type of event. For instance, graph 404 shows that event A occurs regularly at certain time intervals. In the illustrated example, event A occurs at almost the same time interval during the time window $t_0$ to $t_1$ and, therefore, is unlikely to correspond to an indicator of the patient's status. For instance, uniform log data, such as that illustrated by event A, most likely corresponds to some periodic check or routine action by a caregiver. On the other hand, event B and event C are non-uniform type events, which occur at irregular time intervals in the time window $t_0$ to $t_1$. To generate combined features from sensor data and log data for predicting the target status, changing points of status are significant. In some examples herein, the non-uniform events in the log data are considered to be indicators of points in time at which the patient status changed.

As mentioned above, the management application may aggregate the sensor data and the log data for a particular time window, and may then distinguish between events in the log data that appear uniform and events in the log data that appear to be non-uniform. As one example for distinguishing between uniform events and non-uniform events, the management application may apply a clustering technique for two clusters with features of mean and standard deviation of time intervals for each event. Example clustering techniques and other classifying techniques include nearest neighbor algorithms, distance functions, and other connectivity-based clustering algorithms.

As one example, the management application may determine a plurality of events of different event categories. For example, event A may be categorized as a routine check of patient temperature and blood pressure; event B may be categorized as administration of medicine through an IV; and event C may be categorized as changing a treatment device setting, or the like. Each occurrence of each event category may have a time associated with that occurrence. The management application may determine a standard deviation of the timing of each occurrence of each event for each event category, and may classify events associated with a standard deviation less than a threshold standard deviation as uniform events, and events associated with a standard deviation greater than the threshold standard deviation as non-uniform events.

In the illustrated example, the management application may determine that standard deviation for the timings of event A is below the standard deviation threshold, while the standard deviations for the timings of occurrences of events B and C are outside the standard deviation threshold. Accordingly, event A may be classified as uniform and event B and C may be classified as non-uniform. Numerous other algorithms and techniques for distinguishing uniform events from non-uniform events will be apparent to those of skill in the art having the benefit of the disclosure herein.

Figure 5:
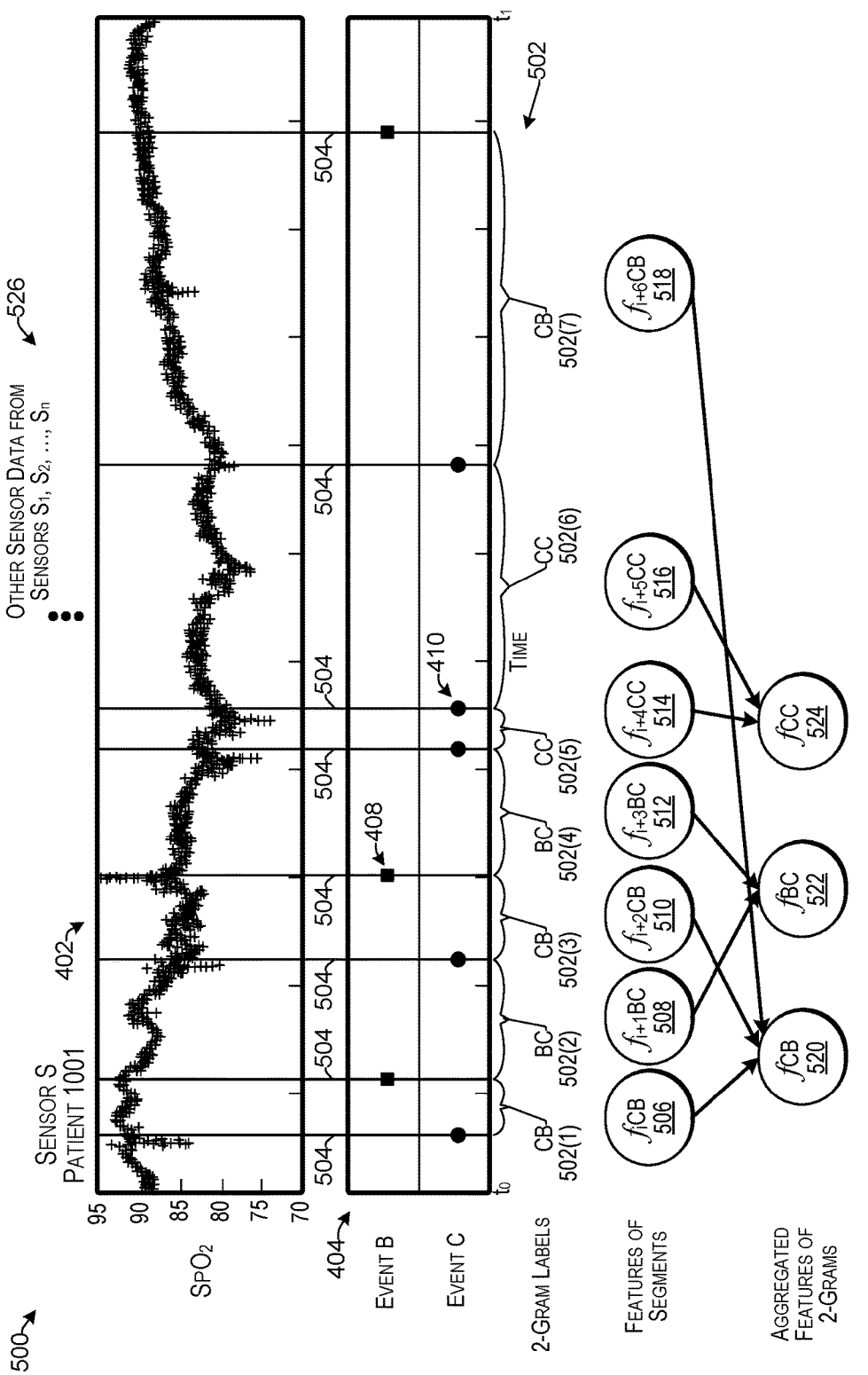
FIG. 5 illustrates an example of segmentation and labeling of data according to some implementations.

FIG. 5 illustrates an example 500 of segmentation and labeling of data according to some implementations. For instance, the feature vectors herein may be determined directly from the sensor data and log data, as discussed with respect to FIG. 5, or may be determined indirectly using a computational model, as discussed with respect to FIGS. 6 and 7. In this example, the sensor data 402 and the log data 404 corresponding to the non-uniform events identified in FIG. 4, namely event B and event C, is divided into a plurality of time segments 502 based on the time of event occurrence. Thus, the uniform event A is excluded from use in determining the feature vector. Vertical lines 504 illustrate lines of division between the time segments 502. Each time segment 502 may be labeled with an N-gram label indicating an order of event occurrence. In this example, there are two non-uniform events, so 2-gram labels are used, with the first letter indicating the start event of the time segment and the second letter indicating the end event of the time segment. For instance, a first time segment 502(1) from the first occurrence of event C to a first occurrence of event B is labeled CB; a second time segment 502(2) from the first occurrence of event B to the second occurrence of event C is labeled BC; a third time segment 502(3) from the second occurrence of event C to the second occurrence of event B is labeled CB; a fourth time segment 502(4) from the second occurrence of event B to the third occurrence of event C is labeled BC; a fifth time segment 502(5) from the third occurrence of event C to the fourth occurrence of event C is labeled CC; a sixth time segment 502(6) from the fourth occurrence of event C to the firth occurrence of event C is labeled CC; and a seventh time segment 502(7) from the fifth occurrence of event C to the third occurrence of event B is labeled CB.

Features are generated for each segment 502 based on sensor values within that respective segment. Accordingly, features $f_iCB$ 506 are generated from time segment 502(1); features $f_{i+1}BC$ 508 are generated from time segment 502(2); features $f_{i+2}CB$ 510 are generated from time segment 502(3); features $f_{i+3}BC$ 512 are generated from time segment 502(4); features $f_{i+4}CC$ 514 are generated from time segment 502(5); features $f_{i+5}CC$ 516 are generated from time segment 502(6); and features $f_{i+6}CB$ 518 are generated from time segment 502(7). Subsequently, the features of the time segments 502 are aggregated (for example, summed together) for each N-gram in the time window to generate aggregated features fCB 520, fBC 22, and fCC 524.

As an example, for the generation of features in the respective segments, statistical metrics such as the mean, median, standard deviation, or the like, may be used. For example, the features $f_iCB$ 506 that are generated from segment 502(1) may include the mean, median, and standard deviation of the sensor S data points between the first occurrence of event C and the first occurrence of event B. Furthermore, the features $f_iCB$ 506 may include the mean, median, and standard deviation of data received from numerous other sensors for the same patient 1001 during this time segment 502(1). For example, as indicated at 526, the sensor data may also include sensor data from a plurality of sensors $S_1, S_2, \ldots, S_n$, measured over the selected time window. The mean, median, and/or standard deviation for each time segment 502 may be calculated for the sensor data for each sensor $S_1, S_2, \ldots, S_n$, and included as part of the features for that time segment 502. Accordingly, the features $f_iCB$ 506 for the time segment 502(1) may include features corresponding to a plurality of sensors associated with the patient 1001. The features for the other time segments 502(2)-502(7) may be similarly calculated.

Subsequently, the features for each sensor S and $S_1, S_2, \ldots, S_n$ may be combined according to the time segment labels to obtain the aggregated features fCB 520, fBC 522, and fCC 524. For example, for aggregating features into fCB 520, the features for sensor S, e.g., the mean for sensor S at segment 502(1), the mean for sensor S at segment 502(3) and the mean for sensor S at segment 502(7) may be combined to determine an overall mean for sensor S the time segments labeled CB. The means for other sensors $S_1, S_2, \ldots, S_n$ in these time segments may be similarly combined for the respective sensor. In addition, the median and standard deviation at segments 502(1), 502(3), and 502(7) for each sensor may be similarly combined according to sensor, such as based on the average of these values. The aggregation of the features fBC 522 and fCC 524 may be similarly performed.

After the features have been aggregated for the respective N-grams to obtain the aggregated features fCB 520, fBC 522, and fCC 524, the features of the N-grams may be concatenated into a feature vector f, e.g., f=[fCB, fBC, fCC . . . ]. The condition of the patient may then be predicted based on the feature vector f using any machine learning algorithms that have the capability of either classification or regression. Typically, the computational models and the computed feature vectors may be used with machine learning algorithms such as Logistic Regression, Support Vector Machine, etc., and those algorithms may provide classification or regression results. For instance, to avoid oxygen toxicity, a patient's fraction of inspired oxygen ($FiO_2$) may need to be reduced as soon as possible. The control of the patient's $FiO_2$ may be controlled by controlling a ventilator setting based on patient's status as represented by one or more feature vectors f. Therefore, the regression may be performed based on the suitable values of $FiO_2$ and related parameters of ventilators. By forming a feature vector f, as described above, the features may be distinguished based on the occurrences of non-uniform events, which may correspond to non-uniform sensor data in some cases. Accordingly, this technique may increase the accuracy of prediction and/or estimation of states of the target, because the occurrences of non-uniform data may correspond to points at which the state of the patient changes.

When ground-truth data regarding target estimation/prediction, which corresponds with all, or a subset of, the computational feature vector is provided, the machine learning algorithms, such as in the above examples, may be used to compute the computational models with the computed feature vectors. For instance, to predict future $FiO_2$ values at certain times, the target values may be determined for the certain times based on past data. Thus, the computational model may be learned from the prior computational feature vectors and the posterior $FiO_2$ values.

Figure 6:
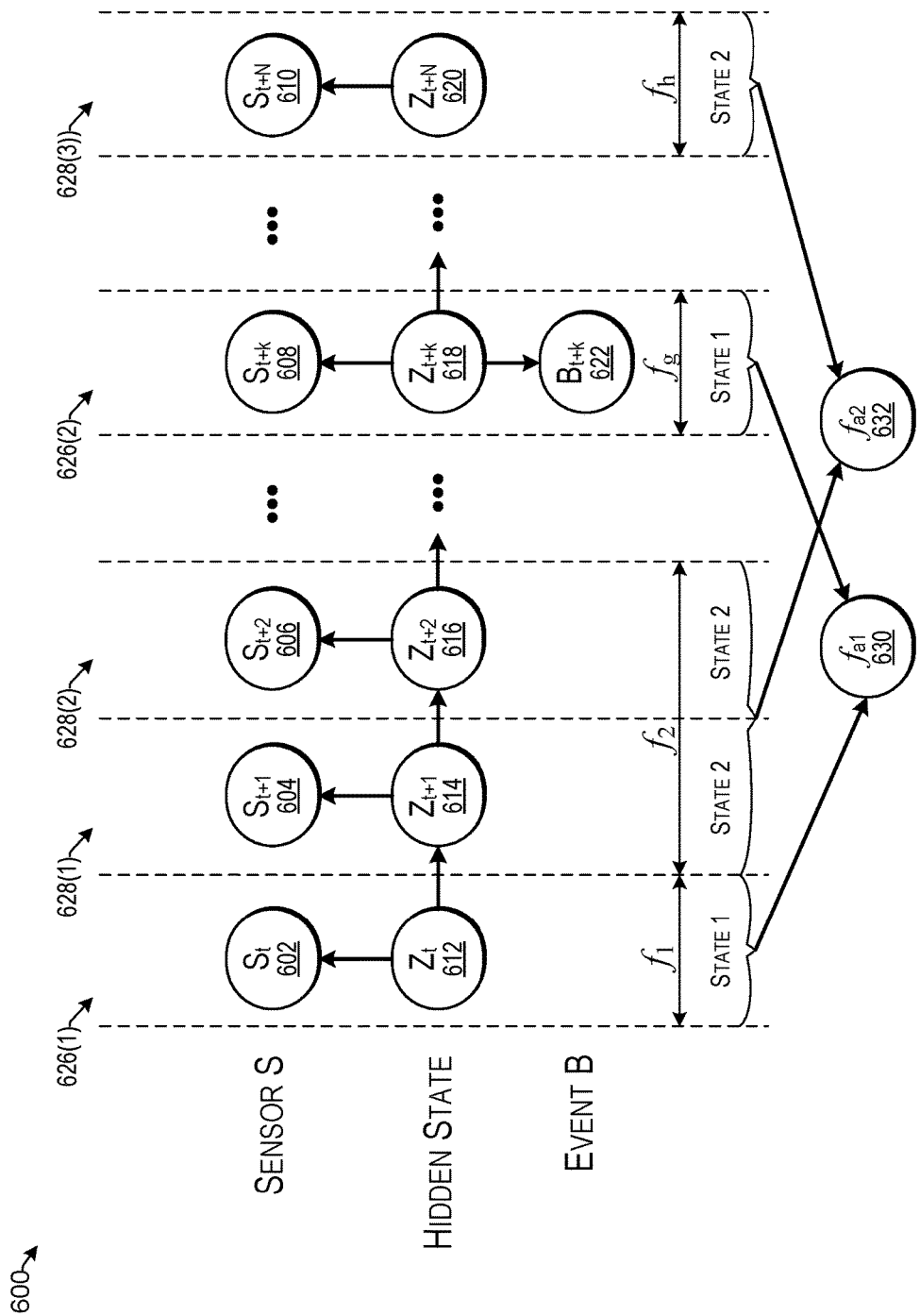
FIG. 6 illustrates an example of a statistical model according to some implementations.

FIG. 6 illustrates an example of a Hidden Markov Model (HMM) 600 according to some implementations. As mentioned above, the example discussed with respect to FIG. 5 provides an example of directly determining combined features based on received sensor data and log data for a target. The examples of FIGS. 6 and 7 describe examples of indirect techniques for determining the combined features by employing trained computational models to perform the analysis. The HMM 600 is one example of a computational model that may be used for determining combined features based on received sensor data and log data for a patient; however, other types of computational models may be used in other examples, as enumerated above. Further, for ease of explanation, the example HMM 600 is configured to describe only one sensor series and one type of non-uniform event; however, numerous other sensors and non-uniform events may be included in the HMM 600 in other examples.

The HMM 600 includes hidden states $Z_t$ to $Z_{t+N}$, sensor observations $S_t$ to $S_{t+N}$ and an event observation of $B_{t+k}$. The sensor observations include $S_t$ 602, $S_{t+1}$ 604, $S_{t+2}$ 606, ... $S_{t+k}$ 608 ... to $S_{t+N}$ 610. Furthermore, the hidden state includes $Z_t$ 612, $Z_{t+1}$ 614, $Z_{t+2}$ 616, ... $Z_{t+k}$ 618 ... to $Z_{t+N}$ 620. Additionally, event B includes an event observation $B_{t+k}$ 622. As one example, each change in the hidden state, such as the change from $Z_t$ 612 to $Z_{t+1}$ 614, may correspond to an occurrence of the non-uniform event B. The HMM 600 may be trained using training data, as discussed above, such as by using the historical sensor data and the historical log data from a plurality of patients. The historical sensor data may be classified into uniform events and non-uniform events, and the uniform events may be excluded from use in training the HMM 600. After the HMM 600 has been trained, sensor data and log data received for a particular patient may be analyzed using the HMM 600 to determine combined features, such as a feature vector.

In some examples, the production probability distribution for the sensor S may be a Gaussian distribution. For instance, most sensor values may be real numbers mathematically. Therefore, a production probability of the event B may be a discrete probability, which corresponds to the frequency of occurrence of each event value for event B. Furthermore, because the HMM 600 does not include a loop structure, the sum-product algorithm may be applied to estimate each hidden state $Z_t$ 612 to $Z_{t+N}$ 618. For instance, the sum-product algorithm is an estimate algorithm for hidden Markov models that computes the posterior marginal distributions of latent parameters of hidden Markov models.

Further, the max-sum algorithm may be applied for determining the most likely states. For instance, given a sequence of observations $S_{t:t+N} := S_t, \ldots, S_{t+N}$, by using the estimated latent parameters, the max-sum algorithm computes, for all hidden state variables $Z_k \in \{Z_t, \ldots Z_{t+N}\}$, the maximum likelihood estimation on $Z_k$ by maximized distribution $P(Z_k|S_{t:t+N})$. The max-sum algorithm makes use of the principle of dynamic programming to compute efficiently the values that are required to obtain the posterior marginal distributions in two passes. In general HMM cases, the first pass may go forward in time, while the second pass may go backward in time.

The max-sum algorithm may be applied to use training data 130 for training the HMM by updating each parameter in the HMM. For instance, let a distribution $P(S_t|Z_k)$ be a Gaussian distribution, and then the Gaussian distribution can be represent by two parameters such as mean (u_z) and standard deviation (s_z). State transition probabilities may also be parameters. In some examples, the number of states may be given and not a parameter to be learned. The max-sum algorithm may find most or local most likely parameters with training data.

As one example, the management application may determine time segments by concatenating a contiguous same hidden state. For example, time segments 626(1) and 626(2) may correspond to a first hidden state, and time segments 628(1), 628(2), and 628(3) may correspond to a second hidden state. Because the hidden states at time segments 628(1) and 628(2) are the same state, i.e., state 2, and are contiguous, the corresponding time segments may be concatenated when determining the features $f_2$. Accordingly, for each time segment, the management program may calculate features $f_i$(time segment), e.g., f=mean($s_i$), median($s_i$), and/or standard deviation($s_i$), count($z_i$), as discussed above with respect to FIG. 5. Furthermore as indicated at 630 and 632, for each hidden state, the management program may concatenate the aggregated features to obtain a feature vector f.

The estimation of the hidden states $Z_t$ to $Z_{t+N}$ in this example is made more accurate by the use of the non-uniform event B from the log data in addition to the sensor data, as compared to using the sensor data alone. After the hidden states $Z_t$ to $Z_{t+N}$ are estimated, statistical metrics such as the mean, the median, the standard deviation, or the like, can be used to generate features corresponding to each sensor during each hidden state, similar to the technique discussed above in the example of FIG. 5. The transition probabilities of the hidden states $Z_t$ to $Z_{t+N}$ may also be used to generate features. By forming combined features, such as feature vectors, the features may be indirectly distinguished based on the occurrence of non-uniform data corresponding to the occurrence of non-uniform events. As mentioned above, the distinguished features may increase accuracy of prediction and/or estimation of target status because the occurrences of non-uniform data typically correspond to points at which a patient's status changes. Typically, the computational models and the computed feature vectors may be used with machine learning algorithms such as Logistic Regression, Support Vector Machine, etc., and those algorithms may provide classification or regression results. For instance, as in the example discussed above, to avoid oxygen toxicity, a patient's $FiO_2$ may need to be reduced as soon as possible. The control of the patient's $FiO_2$ may be controlled by controlling a ventilator setting based on patient's status as represented by one or more feature vectors f. Therefore, the regression may be performed based on the suitable values of $FiO_2$ and related parameters of ventilators.

When ground-truth data regarding target estimation/prediction, which corresponds with all, or a subset of, the computational feature vector is provided, the machine learning algorithms, such as in the above examples, may be used to compute the computational models with the computed feature vectors. For instance, to predict future $FiO_2$ values at certain times, the target values may be determined for the certain times based on past data. Thus, the computational model may be learned from the prior computational feature vectors and the posterior FiO2 values.

Figure 7:
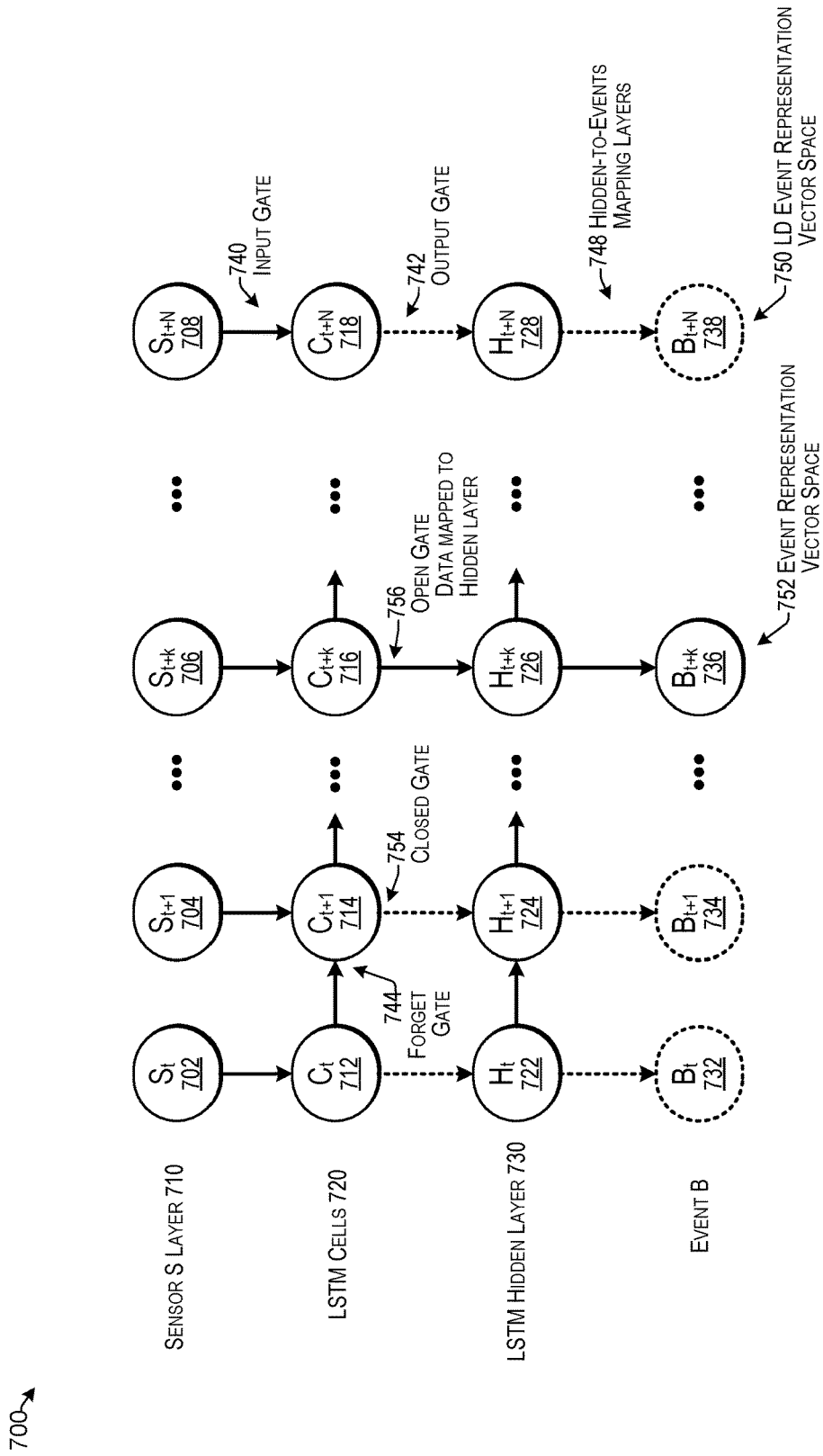
FIG. 7 illustrates an example structure of an artificial neural network according to some implementations.

FIG. 7 illustrates an example structure of a Recurrent Neural Network (RNN) 700 according to some implementations. For example, such as in the case that there are observed states, an RNN may be used as a computational model instead of, or in addition to, the HMM 600. The RNN 700 in this example has a structure referred to as "Long-Short-Term-Memories" (LSTMs). For instance, the RNN 700 may be used to learn from experience for classifying and predicting time series when there are time lags of unknown size between important events, e.g., the non-uniform events herein. In this example, the RNN 700 includes sensor observations $S_t$ 702, $S_{t+1}$ 704, ... $S_{t+k}$ 706 ... to $S_{t+N}$ 708. In addition, LSTM cells include $C_t$ 712, $C_{t+1}$ 714, ... $C_{t+k}$ 716 ... to $C_{t+N}$ 718. Furthermore, an LSTM hidden layer includes $H_t$ 722, $H_{t+1}$ 724, ... $H_{t+k}$ 716 ... to $H_{t+N}$ 728. Additionally, event B layer includes $B_t$ 732, $B_{t+1}$ 734, ... $B_{t+k}$ 736 ... to $B_{t+N}$ 738. The cell $C_{t+N}$ 718 may indicate end states of the target that can be used as features.

The RNN 700 may include at least six components, namely, input gates 740 that lead into LSTM cells, output gates 742 that lead out of LSTM cells, forget gates 744, the LSTM cells 712-718, inputs from sensor S 702-708, and outputs to the LSTM hidden layer 730. The RNN 700 shown in FIG. 7 has an additional component, namely, a hidden-to-events mapping layer 748. The hidden-to-events mapping layer 748 may include two mapping functions, namely, a first linear mapping function to map from the event name to a low dimensional event representation vector space 750, and a second mapping function to map from the hidden layer 730 to an event representation vector space 752. As indicated at 754, dashed lines may indicate closed gates, while, as indicated at 756, solid lines may indicate open gates. Furthermore, 756 indicates an open gate at which data is mapped to the hidden layer 730.

The RNN 700 may initially be trained using historical log data and sensor data for a plurality of patients as training data, as discussed above with respect to FIG. 1. For example, the historical log data may be classified to identify uniform events and non-uniform events, and to exclude uniform events from the historical log data that is used for training the RNN 700. Following training the RNN 700 may be executed using received sensor data for a target patient for a time window. The RNN 700 may generate features based on the received sensor data at $C_{t+N}$ 718, which may represent the end state of the target patient.

In the example RNN 700 of FIG. 7, a difference with an ordinal LSTM may exist at the output gates 742. For instance, in an ordinal LSTM, the output gates may be controlled by inputs. In the example of FIG. 7, the Sensor S is the input. However, an ordinal LSTM model may not be able to handle the appearance non-uniform data. In the illustrated RNN of FIG. 7, the output gates 742 are controlled by the events, i.e., Event B in this example, rather than the inputs 702-708 from the Sensor S. Thus, the hidden layer 730 may have a function of controlling whether the event B is observed. In this configuration, the non-uniform appearance of the events can be accommodated by the RNN 700.

A cost function that may be minimized when training the RNN 700 may be expressed as follows:

$$J(u) = \sum_t p(v_t^T u_t \mid v^T u_t)$$

Where u is the vector from the hidden layer 730 of each time t, and v is the vector from the event representation vector from the event B of each time t, e.g., corresponding to $B_{t+k}$ 736. Further, the probability p( ) is the probability of a given condition. As an actual probability p measure, a softmax function may be used, e.g., as follows:

$$\text{softmax } p(v_t^T u_t \mid v^T u_t) = \frac{\exp(v_t^T u_t)}{\sum_{e \in Event} \exp(v_e^T u_t)}$$

Alternatively, because the computational cost of the above softmax function may be expensive in some examples, a negative sampling loss function may be used instead of the softmax function. By executing the RNN 700, the cell $C_{t+N}$ 718 may produce combined features that may be indirectly distinguished based on the occurrence of non-uniform data corresponding to the occurrence of non-uniform events, i.e., event B in this example, which is from the historical log data used to train the RNN 700.

Any machine learning algorithms that have the capability of either classification or regression may be applied to the feature vector for determining the analysis results. Typically, the computational models and the computed feature vectors may be used with machine learning algorithms such as Logistic Regression, Support Vector Machine, etc., and those algorithms may provide classification or regression results. In addition to those algorithms, RNN 700 may be used as a pre-trained network, and may provide a pipeline from sensor and log data to classification and/or regression results. As an example of a use-case, as in the example discussed above, to avoid oxygen toxicity, a patient's $FiO_2$ may need to be reduced as soon as possible. The control of the patient's $FiO_2$ may be controlled by controlling a ventilator setting based on patient's status as represented by one or more feature vectors f. Therefore, the regression may be performed based on the suitable values of $FiO_2$ and related parameters of ventilators.

When the analysis result has been determined, the analysis result may be stored in the computer-readable media of FIG. 1. Further, one or more of the target machines described with respect to FIG. 1 may be controlled by the management application based on the analysis result. For example, suppose that the analysis result is an estimation of the respiratory status of the particular patient, and the particular patient is currently on a mechanical ventilator. Accordingly, the management application may change the ventilator setting, such as the inspiratory pressure setting, based on the determined respiratory status of the particular patient. As another example, if the analysis result is a determination with respect to a state of the patient, such as a prediction as to whether a patient should be placed on a mechanical ventilator within an hour, the analysis result may be sent for display on any of the displays discusses above with respect to FIG. 1, and a notification may be sent to a caregiver to take action, such as preparing a ventilator for the patient based on the analysis result.

FIGS. 8-11 are flow diagrams illustrating example processes according to some implementations. The processes are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation. Any number of the described blocks can be combined in any order and/or in parallel to implement the process, or alternative processes, and not all of the blocks need be executed. For discussion purposes, the processes are described with reference to the environments, frameworks and systems described in the examples herein, although the processes may be implemented in a wide variety of other environments, frameworks and systems.

Figure 8:
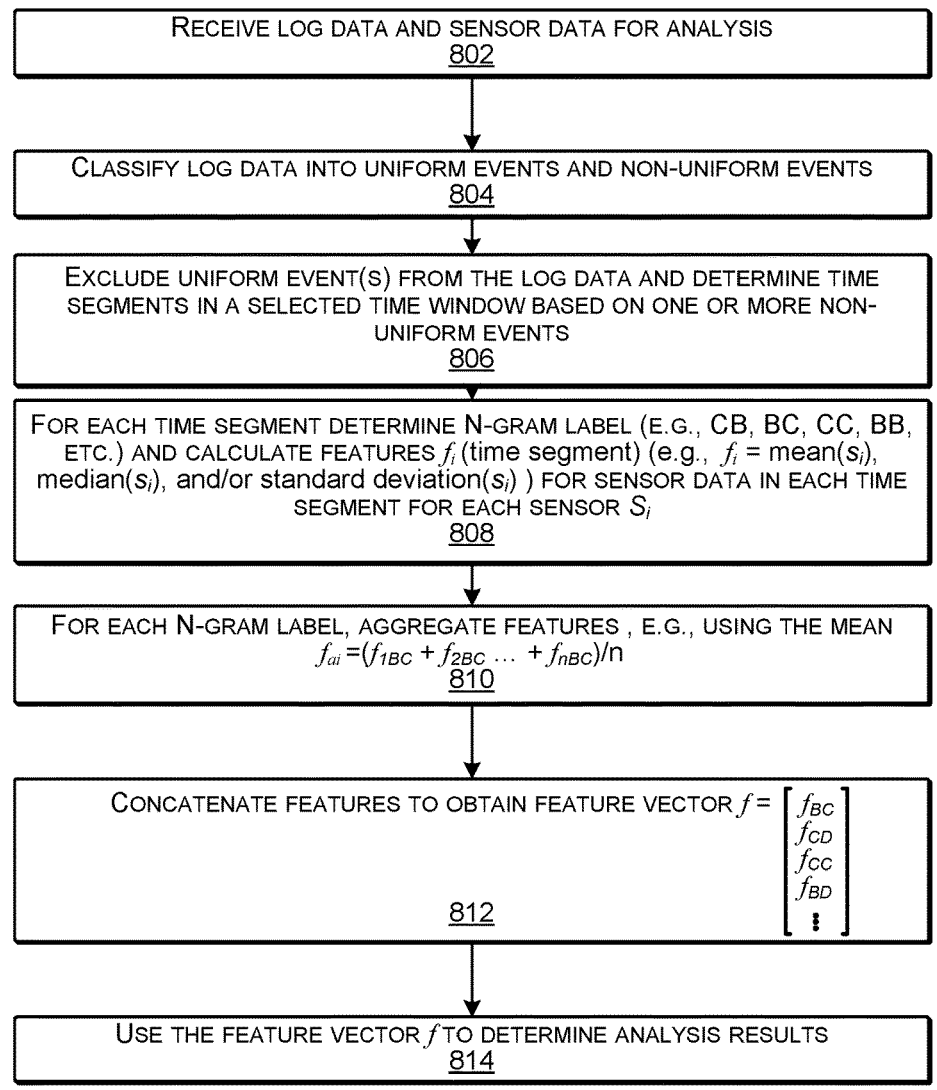
FIG. 8 is a flow diagram illustrating an example process for directly determining features according to some implementations.

FIG. 8 is a flow diagram illustrating an example process 800 including a direct technique for determining a feature vector according to some implementations. In some examples, the process 800 may be executed by the service computing device 102 or other suitable computing device.

At 802, the computing device may receive log data and sensor data. For example, the computing device may receive log data and sensor data relating to a target, such as patient. At 804, the computing device may classify the log data into uniform events and non-uniform events. For example, the computing device may determine a plurality of events of different event categories. Each occurrence of each event category may be associated with a time. Further, the computing device may determine a standard deviation of the timing of each occurrence of each event for each event category. Next, the computing device may classify events associated with a standard deviation less than a threshold standard deviation as uniform events, and may classify events associated with a standard deviation greater than the threshold standard deviation as non-uniform events.

At 806, the computing device may exclude one or more uniform events from the log data and may determine time segments based on the non-uniform events in the log data. As one example, the time segments may correspond to the time between an occurrence of one event, and the occurrence of another event within a selected time window for the data being analyzed.

At 808, for each time segment (e.g., CB, BC, CC, BB, etc.) and for each sensor data $S_i$, the computing device may calculate features $f_i$(time segment) e.g., $f_i$=mean ($s_i$), median ($s_i$), and/or standard deviation ($s_i$).

At 810, for each N-gram label, the computing device may aggregate $f_i$, e.g., using the mean $(f_{1BC}+f_{2BC} \ldots +f_{nBC})/n$.

At 812, the computing device may concatenate the aggregated features to obtain a feature vector $f=[f_{BC}, f_{CD}, f_{CC}, f_{BD} \ldots]$.

At 814, the computing device may use the feature vector to determine an analysis result, such as a prediction or estimation about the patient.

Figure 9:
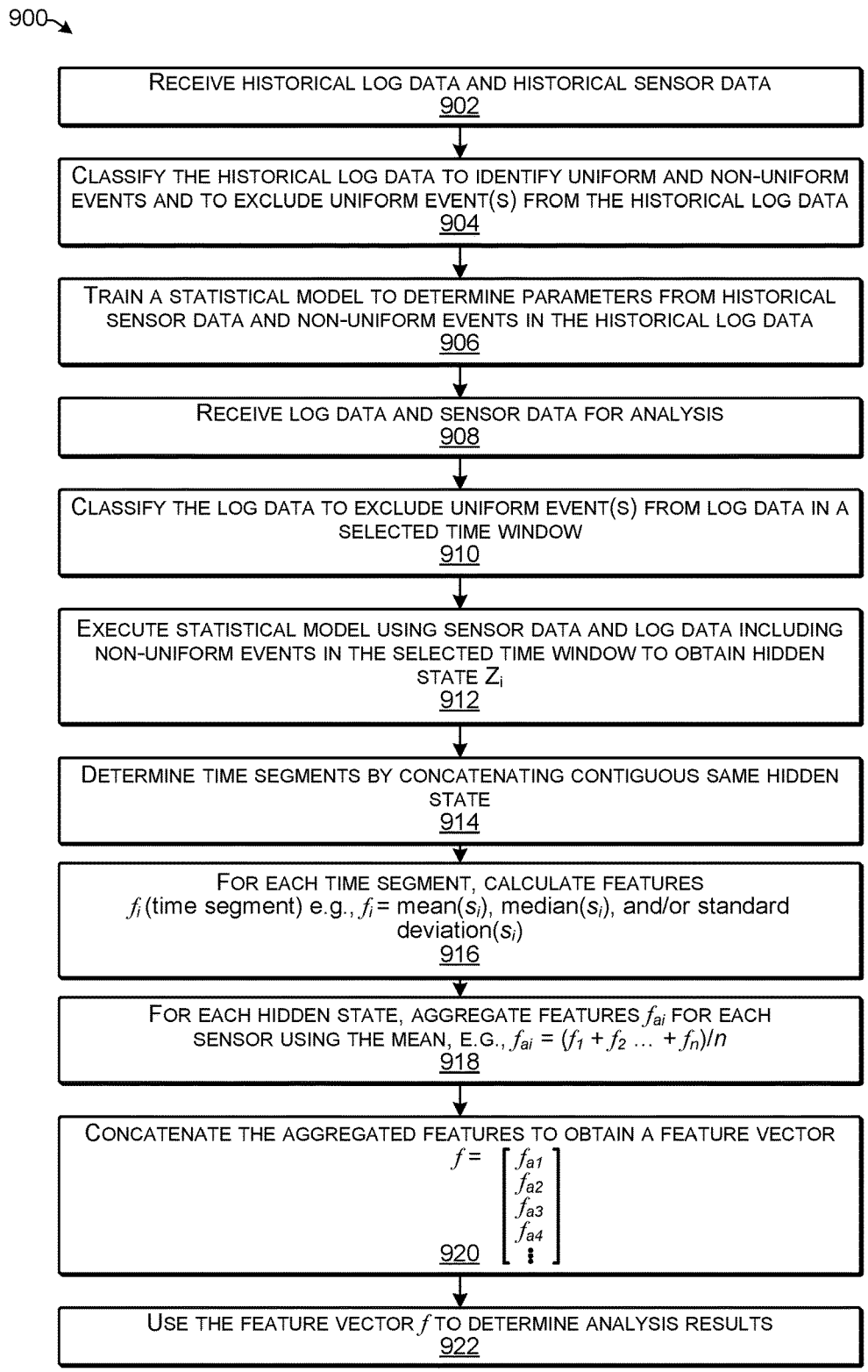
FIG. 9 is a flow diagram illustrating an example process for indirectly determining features according to some implementations.

FIG. 9 is a flow diagram illustrating an example process 900 including an indirect technique for determining a feature vector according to some implementations. In some examples, the process 900 may be executed by the service computing device 102 or other suitable computing device. In this example, blocks 902-906 may correspond to a training phase, while blocks 908-922 may correspond to an application phase.

At 902, the computing device may receive historical log data and historical sensor data. For example, the computing device may receive historical log data and historical sensor data that has been stored for a plurality of patients.

At 904, the computing device may classify the historical log data to exclude uniform event(s) from the historical log data. For example, the computing device may determine a plurality of events in the historical log data, and may classify the events as either uniform events or non-uniform events to determine at least one non-uniform event. Furthermore, in some cases, the computing device may exclude data of at least one uniform event when determining the features.

At 906, the computing device may train a statistical model to determine parameters from the historical sensor data and historical log data. As one example, the computing device may train a hidden Markov model (HMM) to determine parameters based on the non-uniform events identified from the historical log data and further based on the corresponding historical sensor data.

At 908, the computing device may receive log data and sensor data for analysis. For example, the computing device may receive log data and sensor data from sensors associated with a particular target, such as a particular patient. Further, the computing device may receive log data recorded by a logger, such as a nurse or other caregiver.

At 910, the computing device may classify the log data into uniform events and non-uniform events to exclude one or more uniform events from the log data in a selected time window. For example, the computing device may determine a plurality of events in the log data, and may classify the events as either uniform events or non-uniform events to determine at least one non-uniform event. Furthermore, in some cases, the computing device may exclude data of at least one uniform event when determining the features.

At 912, the computing device may execute the statistical model using the sensor data in the time window and non-uniform event data from the log data in the selected time window to obtain a hidden state $Z_i$.

At 914, the computing device may determine time segments by concatenating contiguous same hidden states, if any.

At 916, for each time segment, the computing device may calculate features $f_i$(time segment) e.g., $f_i$=mean ($s_i$), median ($s_i$), and/or standard deviation ($s_i$).

At 918, the computing device may, for each matching hidden state, aggregate $f_i$ using the mean, e.g., $f_{a1}=(f_1+ \ldots, f_g)/g$. In other words, for the same hidden state, the computing device may aggregate the features and determine an average of each aggregated feature for each different sensor and each different hidden state.

At 920, the computing device may concatenate features from the aggregated features to obtain a feature vector $f=[f_{a1}, f_{a2}, f_{a3}, f_{a4} \ldots]$.

At 922, the computing device may use the feature vector to determine an analysis result, such as a prediction or estimation about the patient.

Figure 10:
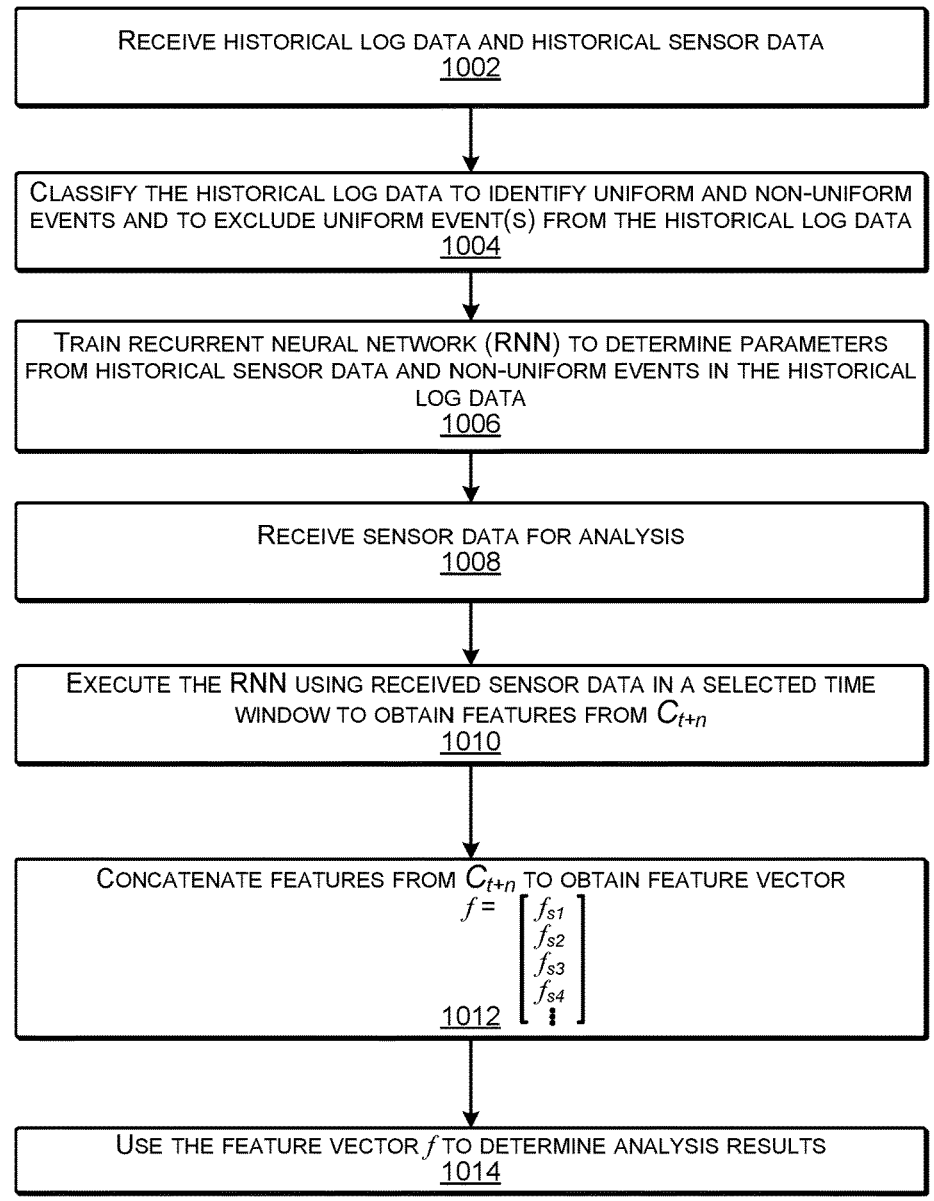
FIG. 10 is a flow diagram illustrating an example process for indirectly determining features according to some implementations.

FIG. 10 is a flow diagram illustrating an example process 1000 including an indirect technique for determining a feature vector according to some implementations. In some examples, the process 1000 may be executed by the service computing device 102 or other suitable computing device. In this example, blocks 1002-1006 may correspond to a training phase, while blocks 1008-1014 may correspond to an application phase.

At 1002, the computing device may receive historical log data and historical sensor data. For example, the computing device may receive historical log data and historical sensor data that has been stored for a plurality of patients.

At 1004, the computing device may classify the historical log data to exclude uniform event(s) from the historical log data used for training. For example, the computing device may determine a plurality of events in the historical log data, and may classify the events as either uniform events or non-uniform events to determine at least one non-uniform event. Furthermore, in some cases, the computing device may exclude data of at least one uniform event when determining the feature vector.

At 1006, the computing device may train a recurrent neural network (RNN) to determine parameters (i.e., weights) from historical sensor data and non-uniform events in the historical log data.

At 1008, the computing device may receive sensor data for analysis the sensor data corresponding to a selected time window.

At 1010, the computing device may execute the RNN using current received sensor data in a selected time window to obtain features from $C_{t+n}$.

At 1012, the computing device may the computing device may concatenate features obtained from $C_{t+n}$ to obtain a feature vector $f=[f_{s1}, f_{s2}, f_{s3}, f_{s4} \ldots]$.

At 1014, the computing device may use the feature vector f to determine an analysis result, such as a prediction or estimation about the patient.

Figure 11:
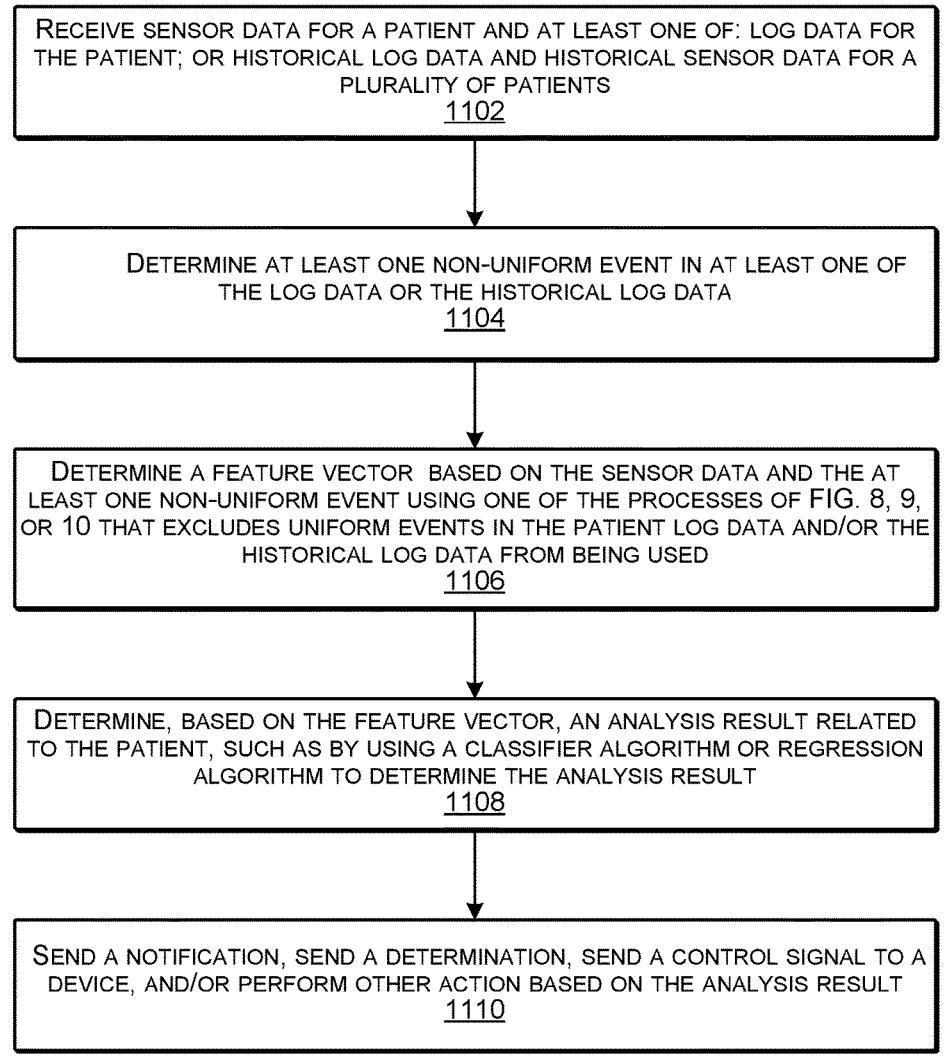
FIG. 11 is a flow diagram illustrating an example process for performing an action based on sensor data and log data according to some implementations.

FIG. 11 is a flow diagram illustrating an example process 1100 for controlling a device and/or sending a notification or determination according to some implementations. In some examples, the process 1100 may be executed by the service computing device 102 or other suitable computing device.

At 1102, the computing device may receive sensor data for a patient and at least one of: log data for the patient; or historical log data and historical sensor data for a plurality of patients.

At 1104, the computing device may determine at least one non-uniform event in at least one of the log data or the historical log data. For example, the computing device may determine a plurality of events in the at least one of the log data or the historical log data, and may classify the events as either uniform events or non-uniform events to determine at least one non-uniform event. In some cases, the computing device may exclude data of at least one uniform event when determining the feature vector.

At 1106, the computing device may determine a feature vector based on the sensor data and at least one non-uniform event using one of the processes of FIG. 8, 9, or 10 that excludes uniform events in the patient log data and/or the historical log data from being used.

At 1108, the computing device may determine, based on the feature vector, an analysis result related to the patient, such as by using a classifier algorithm or regression algorithm to determine the analysis result.

At 1110, the computing device may send a notification, send a determination, send a control signal to a device, and/or perform other action based on the output of the statistical model. As one example, the computing device may send a notification to the logger computing device and/or the facility computing device. For instance, the computing device may send a notification to cause an alert to be presented on a display of the caregiver device and/or a display of the facility computing device. The notification may alert the caregiver to take corrective action and/or may perform other appropriate intervention.

As another example, the computing device may send a determination to another computing device. For instance, the determination may include a prediction regarding the first patient such as whether the first patient is likely to be readmitted in the near future to the care facility, the likelihood of the first patient requiring a particular treatment, or other desired information about the first patient.

Additionally, or alternatively, as another example, the computing device may send a signal to control a target device, such as a treatment device and/or a monitoring device. For instance, the computing device may send a control signal to control a treatment device at the target location. In some cases, the computing device may turn on, turn off, or adjust a setting of a target device, such as a treatment device or a monitoring device. A notification to a caregiver may also be sent in addition to sending the control signal to a target device. Further, in some examples, the control signal may only be sent to the target device in certain situations, such as if a threshold level of urgency is determined.

The example processes described herein are only examples of processes provided for discussion purposes. Numerous other variations will be apparent to those of skill in the art in light of the disclosure herein. Further, while the disclosure herein sets forth several examples of suitable frameworks, architectures and environments for executing the processes, the implementations herein are not limited to the particular examples shown and discussed. Furthermore, this disclosure provides various example implementations, as described and as illustrated in the drawings. However, this disclosure is not limited to the implementations described and illustrated herein, but can extend to other implementations, as would be known or as would become known to those skilled in the art.

Various instructions, processes, and techniques described herein may be considered in the general context of computer-executable instructions, such as program modules stored on computer-readable media, and executed by the processor(s) herein. Generally, program modules include routines, programs, objects, components, data structures, executable code, etc., for performing particular tasks or implementing particular abstract data types. These program modules, and the like, may be executed as native code or may be downloaded and executed, such as in a virtual machine or other just-in-time compilation execution environment. Typically, the functionality of the program modules may be combined or distributed as desired in various implementations. An implementation of these modules and techniques may be stored on computer storage media or transmitted across some form of communication media.

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

What is claimed:

1. A system comprising:
one or more processors; and
one or more non-transitory computer-readable media maintaining executable instructions, which, when executed by the one or more processors, program the one or more processors to perform operations comprising:
receiving sensor data for a patient and at least one of:
log data for the patient; or
historical log data and historical sensor data for a plurality of patients;
determining at least one event classified as a non-uniform event in at least one of the log data or the historical log data;
determining a feature vector based on the sensor data and the at least one non-uniform event;
determining, based on the feature vector, an analysis result related to the patient; and
sending at least one of:
a notification or determination to a computing device; or
a control signal to a device for controlling a device.

2. The system as recited in claim 1, wherein the operation of determining at least one event classified as the non-uniform event in at least one of the log data or the historical log data comprises:
determining a plurality of events in the at least one of the log data or the historical log data;
classifying events of the plurality of events as either uniform events or non-uniform events to determine the at least one non-uniform event; and
excluding at least one uniform event when determining the feature vector.

3. The system as recited in claim 2, wherein the operation of classifying events of the plurality of events as either uniform events or non-uniform events comprises:
determining a plurality of events of different event categories, each occurrence of each event category associated with a timing;
determining a standard deviation of the timing of each occurrence of each event for each event category; and
classifying events associated with a standard deviation less than a threshold standard deviation as uniform and events associated with a standard deviation greater than the threshold standard deviation as non-uniform.

4. The system as recited in claim 1, wherein the operation of determining the feature vector based on the sensor data and the at least one non-uniform event comprises:
  determining time segments in a time window based on the at least one non-uniform event;
  for each time segment, determining features from the sensor data corresponding to the time segment;
  aggregating the features for time segments corresponding to a same order of occurrence of non-uniform events; and
  determining the feature vector by concatenating the aggregated features for the time segments.

5. The system as recited in claim 4, the operations further comprising:
  for each time segment, determining an N-gram label based on the order of occurrence of the non-uniform events; and
  aggregating the features for the time segments corresponding to a same order of occurrence of non-uniform events by aggregating features corresponding to the same N-gram, wherein the features include at least one of a mean of the sensor data within each time segment, a median of the sensor data within each time segment, or a standard deviation of the sensor data within each time segment.

6. The system as recited in claim 1, the operations further comprising:
  training a statistical model using the historical sensor data and at least one non-uniform event from the historical log data;
  executing the statistical model using the sensor data and at least one non-uniform event from the log data in a selected time window;
  determining time segments based at least in part on a hidden state of the statistical model;
  for each time segment, determining one or more features from the sensor data;
  aggregating the features based on matching hidden states; and
  concatenating the aggregated features to determine the feature vector.

7. The system as recited in claim 1, the operations further comprising:
  training a neural network using the historical sensor data and at least one non-uniform event from the historical log data;
  executing the neural network using the sensor data in a selected time window to determine one or more features from a cell of the neural network based on the sensor data; and
  concatenating the features to determine the feature vector.

8. A method comprising:
  receiving, by a processor, sensor data for a target and at least one of:
    log data for the target; or
    historical log data and historical sensor data for a plurality of other targets, wherein the log data and the historical log data include information related to the target generated by a human;
  determining at least one event classified as a non-uniform event in at least one of the log data or the historical log data;
  determining combined features based on the sensor data and the at least one non-uniform event; and
  determining, based on the combined features, an analysis result related to the target.

9. The method as recited in claim 8, further comprising:
  determining a feature vector as the combined features;
  determining the analysis result from the combined features based at least in part on at least one of regression or classification applied to the feature vector; and
  based on the analysis result, sending at least one of:
    a notification or determination related to the target to a computing device; or
    a control signal to a device associated with the target for controlling the device.

10. The method as recited in claim 8, further comprising:
  determining a plurality of events in the at least one of the log data or the historical log data;
  classifying events of the plurality of events as either uniform events or non-uniform events to determine the at least one event classified as the non-uniform event; and
  excluding at least one event classified as a uniform event when determining the features.

11. The method as recited in claim 8, further comprising:
  determining time segments in a time window based on occurrences of a plurality of non-uniform events;
  for individual time segments, determining features from the sensor data corresponding to the time segment;
  aggregating the features according to time segments that correspond to a same order of occurrence of non-uniform events; and
  determining the combined features by concatenating the aggregated features for the time segments.

12. The method as recited in claim 11, further comprising determining the features from the sensor data for the individual time segments by determining at least one of:
  a mean of the sensor data for each time segment,
  a median of the sensor data for each time segment, or
  a standard deviation of the sensor data for each time segment.

13. The method as recited in claim 8, further comprising:
  training a hidden Markov model (HMM) using the historical sensor data and at least one non-uniform event from the historical log data;
  executing the HMM using the sensor data and at least one non-uniform event from the log data in a selected time window;
  determining time segments based at least in part on a hidden state of the HMM;
  for each time segment, determining one or more features from the sensor data;
  aggregating the features based on matching hidden states; and
  concatenating the aggregated features to determine the combined features.

14. The method as recited in claim 8, further comprising:
  training a neural network using the historical sensor data and at least one non-uniform event from the historical log data;
  executing the neural network using the sensor data in a selected time window to determine one or more features from a cell of the neural network based on the sensor data; and
  concatenating the features to determine the combined features.

15. A system comprising:
  one or more processors; and
  one or more non-transitory computer-readable media maintaining executable instructions, which, when executed by the one or more processors, program the one or more processors to:

receive sensor data for a target and at least one of:
- log data for the target; or
- historical log data and historical sensor data for a plurality of other targets;

determine at least one event classified as a non-uniform event in at least one of the log data or the historical log data;

determine a feature vector based on the sensor data and the at least one non-uniform event; and determine, based on the feature vector, an analysis result related to the target.

16. The system as recited in claim 15, wherein, based on the analysis result, the one or more processors are further programmed to send a control signal to a device associated with the target for controlling the device in response to a condition indicated by the analysis result.

17. The system as recited in claim 15, wherein the one or more processors are further programmed to determine at least one event classified as the non-uniform event by:
- determining a plurality of events in the at least one of the log data or the historical log data; and
- classifying events of the plurality of events as either uniform events or non-uniform events to determine the at least one non-uniform event.

18. The system as recited in claim 15, wherein the one or more processors are further programmed to:
- determine time segments in a time window based on the at least one non-uniform event;
- for individual time segments, determine features from the sensor data corresponding to the time segment;
- aggregate the features for time segments corresponding to a same order of occurrence of non-uniform events; and
- determine the feature vector by concatenating the aggregated features for the time segments.

19. The system as recited in claim 15, wherein the one or more processors are further programmed to:
- train a statistical model using the historical sensor data and at least one non-uniform event from the historical log data;
- execute the statistical model using the sensor data and at least one non-uniform event from the log data in a selected time window;
- determine time segments based at least in part on a hidden state of the statistical model;
- for each time segment, determine one or more features from the sensor data;
- aggregate the features based on matching hidden states; and
- concatenate the aggregated features to determine the feature vector.

20. The system as recited in claim 15, wherein the one or more processors are further programmed to:
- train a neural network using the historical sensor data and at least one non-uniform event from the historical log data;
- execute the neural network using the sensor data in a selected time window to determine one or more features from a cell of the neural network based on the sensor data; and
- concatenate the features to determine the feature vector.

* * * * *